(12) United States Patent
Xu

(10) Patent No.: US 8,357,362 B2
(45) Date of Patent: *Jan. 22, 2013

(54) TREATING NON-HEMATOPOIETIC CANCER WITH INTERLEUKIN 6

(75) Inventor: Dawei Xu, Indianapolis, IN (US)

(73) Assignee: Bionewpath LLC, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/490,870

(22) Filed: Jun. 7, 2012

(65) Prior Publication Data

US 2012/0244115 A1 Sep. 27, 2012

Related U.S. Application Data

(63) Continuation of application No. 13/176,093, filed on Jul. 5, 2011, now Pat. No. 8,216,562.

(60) Provisional application No. 61/362,460, filed on Jul. 8, 2010.

(51) Int. Cl.
*A61K 38/20* (2006.01)

(52) U.S. Cl. .......................... 424/85.2; 435/7.1; 435/7.2
(58) Field of Classification Search .................. None
See application file for complete search history.

(56) References Cited

U.S. PATENT DOCUMENTS

| 5,902,576 | A | 5/1999 | Eisenbach et al. |
| 6,348,191 | B1 | 2/2002 | Clark et al. |
| 2007/0207120 | A1 | 9/2007 | Drayton et al. |

OTHER PUBLICATIONS

C. Miyaura et al., FEBS Letters, 234(1):17-21 (1988).
J. Mulé et al., The Journal of Experimental Medicine, 171:629-636 (1990).
J. Mulé et al., The Journal of Immunology, 148(8):2622-2629 (1992).
H. Serve et al., Cancer Res., 51:3862-3866 (1991).
J. Weber et al., J. Immunother Emphasis Tumor Imrnunol. (abstract), 15(4):292-302 (1994).

*Primary Examiner* — Prema Mertz
(74) *Attorney, Agent, or Firm* — Wolf, Greenfield & Sacks, P.C.

(57) ABSTRACT

Use of IL-6 for treating non-hematopoietic cancers, e.g., gp130-negative cancers. Also disclosed is a method for identifying a cancer patient suitable for the IL-6 treatment.

10 Claims, 3 Drawing Sheets

A.

B.

C.
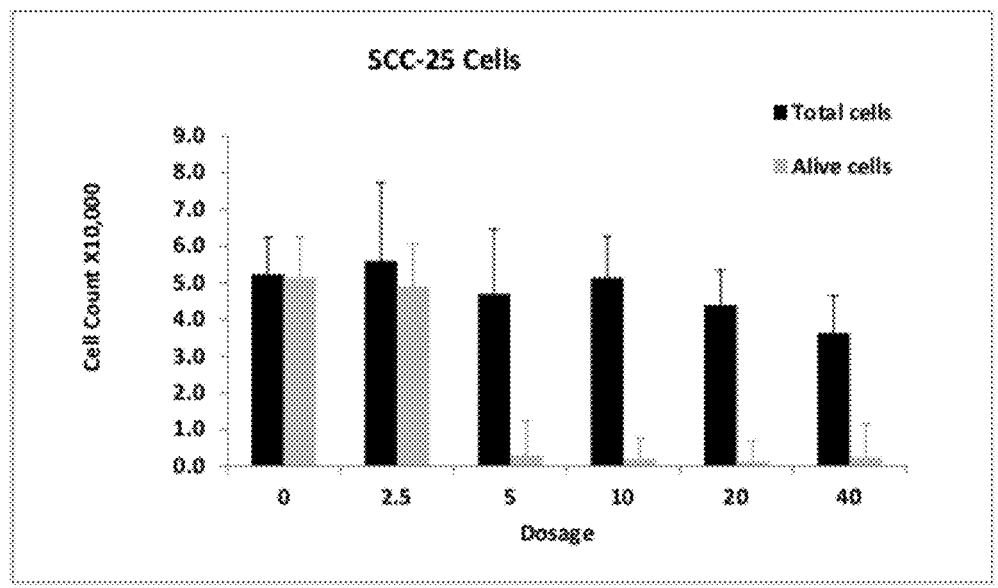
D.
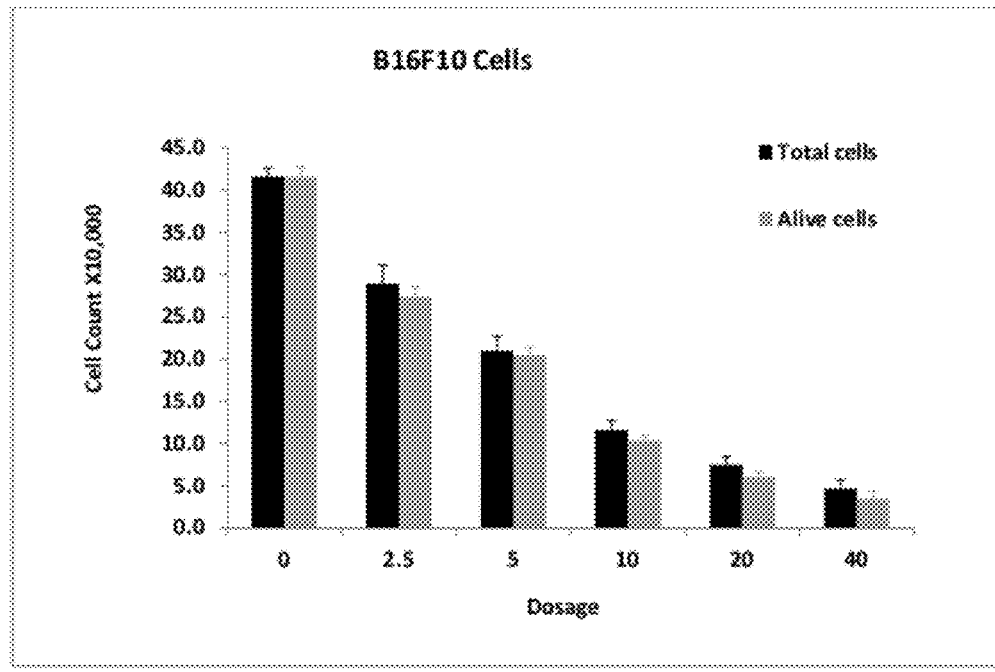

E.
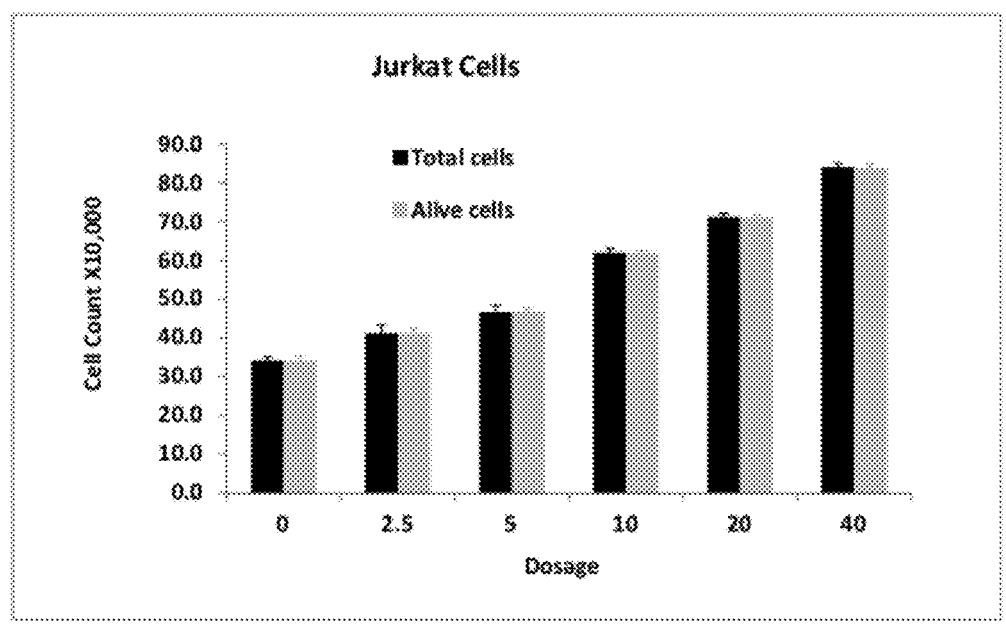

TREATING NON-HEMATOPOIETIC CANCER WITH INTERLEUKIN 6

RELATED APPLICATIONS

This application is a continuation of U.S. patent application Ser. No. 13/176,093, filed Jul. 5, 2011, which claims priority under 35 U.S.C. §119 to U.S. provisional application 61/362,460, filed Jul. 8, 2010. The entire content of all prior applications is herein incorporated by reference in their entirety.

BACKGROUND OF THE INVENTION

Interleukin 6 ("IL-6") is a multifunctional cytokine capable of inducing various immune responses. Acting as both a pro-inflammatory and anti-inflammatory cytokine, IL-6 plays an important role in balancing inflammatory responses in the body. Further, it promotes growth and differentiation of hematopoietic cells, e.g., B cells and T cells. IL-6 also facilitates defensive responses against pathogen infection.

Given its function in promoting hematopoietic cell growth, IL-6 is used in treating disorders associated with deficiencies in hematopoietic cells. On the other hand, IL-6 has been found to contribute to the progress of many diseases, e.g., diabetes, atherosclerosis, systemic lupus erythematosus, and cancer, particularly hematopoietic cancer. Thus, IL-6 antagonists are drug candidates for treating these IL-6 associated diseases.

SUMMARY OF THE INVENTION

The present disclosure is based on the unexpected discoveries that IL-6 inhibits growth of non-hematopoietic cancer cells and that gp130 serves as a biomarker for identifying cancers suitable for IL-6 treatment.

One aspect of the present invention features a method for treating a non-hematopoietic cancer by administering to a subject in need thereof an effective amount of a composition containing IL-6 (e.g., human IL-6). In one example, the composition contains IL-6 as the only active anti-cancer agent. In another example, it also contains one or more additional anti-cancer agents.

The subject to be treated by the method of this invention can be a human patient carrying non-hematopoietic cancer cells (e.g., gp130 negative cancer cells). In some embodiments, such a subject can be identified by examining gp130 expression on his or her cancer cells using methods known in the art, e.g., an immune assay.

A non-hematopoietic cancer refers to a cancer derived from non-hematopoietic cells. Examples include, but are not limited to, breast cancer, ovary cancer, cervical cancer, uterus cancer, testicle cancer, prostate cancer, skin cancer, head and neck cancer, stomach cancer, colon cancer, esophagus cancer, gallbladder cancer, kidney cancer, liver cancer, pancreas cancer, non-small cell lung cancer, brain cancer, bone cancer, neuroblastoma, teratoma, renal cellular carcinoma, hepatitis cellular carcinoma, Alveolus adeocarcinoma, and choriocarcinoma.

Another aspect of this invention features a method of identifying a cancer patient suitable for IL-6 treatment. This method includes (i) providing a sample (e.g., a tumor tissue sample) from a cancer patient that contains cancer cells, (ii) detecting gp130 in the sample by, e.g., examining expression of gp130 on the cancer cells using an immune assay, and (iii) determining whether the cancer patient is suitable for IL-6 treatment. Absence of gp130 in the sample (e.g., on the cancer cells) indicates that the cancer patient can be treated with IL-6.

Also within the scope of this invention is a pharmaceutical composition for treating a non-hemotopoietic cancer that contains IL-6 or use of IL-6 in manufacturing a medicament for the treatment of a non-hemotopoietic cancer.

The details of one or more embodiments of the invention are set forth in the description below. Other features or advantages of the present invention will be apparent from the following drawing and detailed description of several examples, and also from the appended claims.

BRIEF DESCRIPTION OF THE DRAWINGS

The drawing is first described.

DETAILED DESCRIPTION OF THE INVENTION

Figure 1:
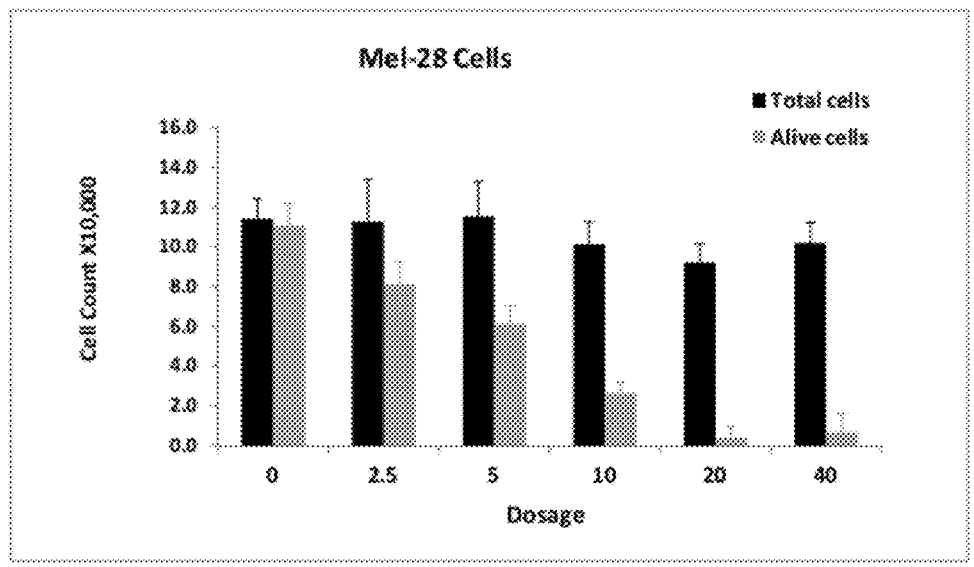
FIG. 1 is a diagram showing that IL-6 inhibits growth of various types of non-hematopoietic cancer cells and promotes growth of a hematopoietic cancer cell, both in a dose-dependent manner.
Figure 1:
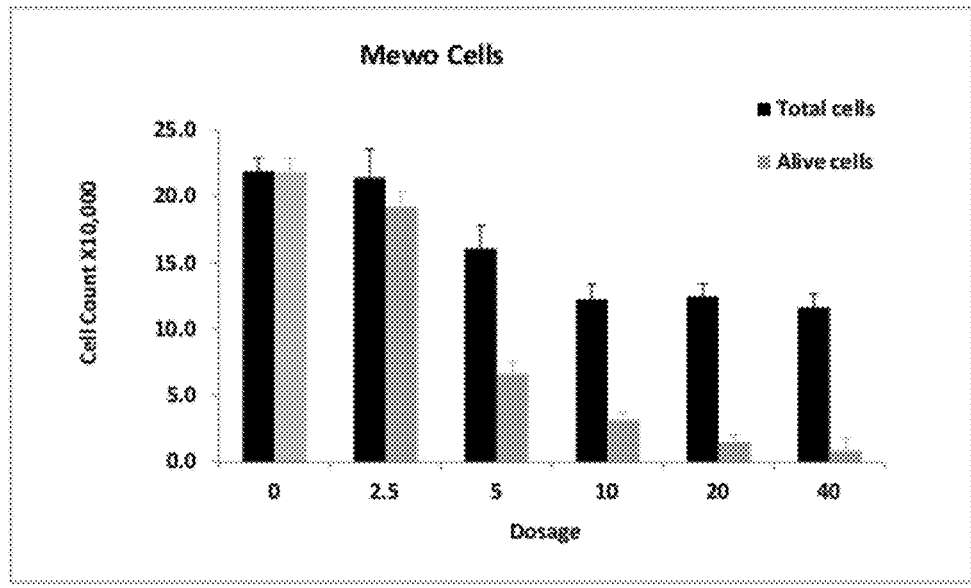

Described herein is a method of treating a non-hematopoietic cancer (e.g., cancers derived from muscle cells, adipose cells, fibrous cells, or bone cells) with an effective amount of a composition containing cytokine IL-6. As used herein, the term "treating" refers to the application or administration of a composition including one or more active agents to a subject, who has a non-hematopoietic cancer, a symptom of the cancer, or a predisposition toward the cancer, with the purpose to cure, heal, alleviate, relieve, alter, remedy, ameliorate, improve, or affect the cancer, the symptoms of the cancer, or the predisposition toward the cancer. "An effective amount" as used herein refers to the amount of each active agent required to confer therapeutic effect on the subject, either alone or in combination with one or more other active it a agents. Effective amounts vary, as recognized by those skilled in the art, depending on route of administration, excipient usage, and co-usage with other active agents.

The IL-6 cytokine to be used in the method of this invention can be a naturally-occurring IL-6 protein, such as that from human, monkey, pig, mouse, or rat. A naturally-occurring IL-6 protein is a polypeptide having the same amino acid sequence as an IL-6 cytokine found in nature, either in mature form or in precursor form. Table 1 below lists a number of exemplary naturally-occurring IL-6 and their GenBank accession numbers. Others can be retrieved from GenBank, e.g., using one of the known IL-6 sequence as a query.

TABLE 1

IL-6 from Various Species and Their GenBank Accession Numbers

| Species | GenBank Accession Number |
|---|---|
| Human IL-6 | NP_000591 (Jun. 15, 2010) |
| Mouse IL-6 | NP_112445 (Jun. 15, 2010) |
| Cattle IL-6 | NP_776348 (Jun. 11, 2010) |
| Pig IL-6 | AAC27127 (Jun. 15, 2010) |
| Rat IL-6 | NP_036721 (Jun. 15, 2010) |
| Monkey IL-6 | AAA99978 (Jun. 10, 2010) |
| Dog IL-6 | NP_001003301 (May 29, 2010) |

Alternatively, the IL-6 cytokine can be a functional variant of a naturally-occurring IL-6. A functional variant of a naturally-occurring IL-6 shares at least 80% (e.g., 85%, 90%, 95%, or 98%) sequence identity to the naturally-occurring counterpart and preserves the same cytokine activity.

The "percent identity" of two amino acid sequences is determined using the algorithm of Karlin and Altschul *Proc. Natl. Acad. Sci.* USA 87:2264-68, 1990, modified as in Karlin and Altschul *Proc. Natl. Acad. Sci. USA* 90:5873-77, 1993. Such an algorithm is incorporated into the NBLAST and XBLAST programs (version 2.0) of Altschul, et al. *J. Mol. Biol.* 215:403-10, 1990. BLAST protein searches can be performed with the XBLAST program, score=50, wordlength=3 to obtain amino acid sequences homologous to the protein molecules of the invention. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NBLAST) can be used.

A functional variant of a naturally-occurring IL-6 can contain conservative mutations inside the essential domains/residue in IL-6 as described above. A mutation is conservative when the amino acids used for the substitutions have structural or chemical characteristics similar to those of the corresponding replaced amino acids. Examples of conservative substitutions can include: substitution of Ala with Gly or Val, substitution of Arg with His or Lys, substitution of Asn with Glu, Gln, or Asp, substitution of Asp with Asn, Glu, or Gln, substitution of Cys with Ser or Ala, substitution of Gin with Asn, Glu, or Asp, substitution of Glu with Gly, Asn, Gln, or Asp, substitution of Gly with Val or Ala, substitution of substitution of Ile with Leu, Met, Val, or Phe, substitution of Leu with He, Met, Val, or Phe, substitution of Lys with His or Arg, substitution of Met with Ile, Leu, Val, or Phe, substitution of Phe with Trp, Tyr, Met, Ile, or Leu, substitution of Ser with Thr or Ala, substitution of Thr with Ser or Ala, substitution of Trp with Phe or Tyr, substitution of Tyr with His, Phe, or Trp, and substitution of Val with Met, Ile, Leu, or Gly.

Conservative mutations in the functional domains would not abolish the cytokine activity of an IL-6 variant. On the other hand, domains not essential to the cytokine activity are tolerable to mutations as amino acid substitutions within these domains are unlikely to greatly affect the activity.

The crystal structure of IL-6 was known in the art, see, e.g., Somer et al., *EMBO J.* 16:989-997 (1997). Moreover, the structure-function relationships of IL-6 were also well-known in the art. See, e.g., Simpson et al., *Protein Science* (1997), 6(5):929-955 (both references are herein incorporated by reference). Based on the crystal structure and known structure-function correlations of IL-6, a skilled artisan can readily identify domains/amino acid residues in an IL-6 protein that are important to its cytokine activity and those that would be tolerable to variations.

A naturally-occurring IL-6 or a functional variant thereof can be prepared via a conventional method, e.g., recombinant technology. See, e.g., U.S. Pat. No. 6,348,191; US Patent Application Publication 2007/0207120; Gething et al., Nature 293:620-625 (1981); and Kaufman et al., Mol Cell. Biol. 5(7):1750-1759 (1985). One example follows. A cDNA fragment encoding an IL-6 protein (either in mature or precursor form) can be obtained from its natural source via, e.g., PCR, and cloned into an expression vector. The expression vector is then introduced into a suitable host cell for expressing the encoded IL-6. When necessary, the IL-6 encoding cDNA can be subjected to codon optimization based on the type of host cells used for producing the IL-6 protein. To increase production/solubility of IL-6, it can be expressed as a fusion protein containing a protein tag. After being purified, the fusion protein can be treated by a protease to remove the protein tag and release the IL-6 protein.

In another example, the whole IL-6 gene can be obtained from its nature source following methods known in the art, e.g., rapid amplification of cDNA (see Schaefer, *Anal Biochem.* 227(2):255-73; 1995) or controlled ribonucleotide tailing of cDNA ends (see Schimidt et al., Nucleic Acids Res. 24(9):1789-91; 1996). The whole IL-6 thus obtained can be cloned into a vector to be introduced into a host cell for producing IL-6 proteins. When necessary, the vector can contain sequences flanking the IL-6 gene that are homologous to sequences at a desired site in a chromosome of the host cell to effect homologous recombination, thereby inserting the IL-6 gene into the host chromosome.

As used herein, a "vector" refers to a nucleic acid molecule capable of transporting another nucleic acid to which it has been linked. The vector can be capable of autonomous replication or integrate into a host DNA. Examples of the vector include a plasmid, cosmid, or viral vector. An expression is a vector in a form suitable for expression of a target nucleic acid in a host cell. Preferably, an expression vector includes one or more regulatory sequences operatively linked to a target nucleic acid sequence to be expressed. The term "regulatory sequence" includes promoters, enhancers, and other expression control elements (e.g., polyadenylation signals). Regulatory sequences include those that direct constitutive expression of a nucleotide sequence, as well as tissue-specific regulatory and/or inducible sequences. The design of the expression vector can depend on such factors as the choice of the host cell to be transformed, the level of transcription of RNA desired, and the like.

The term "promoter" refers to a nucleotide sequence containing elements that initiate the transcription of an operably linked nucleic acid sequence in a desired host cell. At a minimum, a promoter contains an RNA polymerase binding site. It can further contain one or more enhancer it a elements which, by definition, enhance transcription, or one or more regulatory elements that control the on/off status of the promoter. When *E. coli* is used as the host, representative *E. coli* promoters include, but are not limited to, the β-lactamase and lactose promoter systems (see Chang et al., *Nature* 275:615-624, 1978), the SP6, T3, T5, and T7 RNA polymerase promoters (Studier et al., *Meth. Enzymol.* 185:60-89, 1990), the lambda promoter (Elvin et al., *Gene* 87:123-126, 1990), the trp promoter (Nichols and Yanofsky, *Meth. in Enzymology* 101:155-164, 1983), and the Tac and Trc promoters (Russell et al. *Gene* 20:231-243, 1982). When yeast is used as the host, exemplary yeast promoters include 3-phosphoglycerate kinase promoter, glyceraldehyde-3-phosphate dehydrogenase (GAPDH) promoter, galactokinase (GAL1) promoter, galactoepimerase promoter, and alcohol dehydrogenase (ADH) promoter. Promoters suitable for driving gene expression in other types of microorganisms are also well known in the art. Examples of mammalian cell promoters include, but are not limited to, CMV promoter, SV40 promoter, and actin promoter.

Any of the IL-6 proteins, or a DNA plasmid for expressing an IL-6 protein, either alone or in combination with one or more additional anti-cancer agents, can be mixed with a pharmaceutically acceptable carrier to form a pharmaceutical composition, which is free of cells, for use in treating a non-hematopoietic cancer in a subject in need (e.g., a human patient suffering from or at risk for a non-hematopoietic cancer). "Acceptable" means that the carrier must be compatible with the active ingredient of the composition (and preferably, capable of stabilizing the active ingredient) and not deleterious to the subject to be treated. Suitable carriers include microcrystalline cellulose, mannitol, glucose, defatted milk powder, polyvinylpyrrolidone, and starch, or a combination thereof.

As shown in Example 1 below, IL-6 inhibits growth of non-hematopoietic cancer cells and promotes hematopoietic cancer cell growth. In other words, this cytokine is effective in treating a non-hematopoietic cancer while contributes to the progress of a hematopoietic cancer. Thus, to perform the method of this invention, a candidate patient must first be examined to determine that he or she suffers from a non-hematopoietic cancer. Such a patient can be identified via conventional cancer diagnostic methods, e.g., physical examination, blood test, X-ray test, or biopsy.

Alternatively, a patient suitable for the IL-6 treatment described herein can be identified by examining presence/absence of gp130 on cancer cells. Gp130, also known as CD1.30 or IL-6 receptor β chain, is a 130 kDa glycoprotein expressed on various cells. Information about human gp130 can be found in GenBank under accession number NP_002175 (May 23, 2010). To identify a cancer patient suitable for IL-6 treatment, a tissue sample containing cancer cells, obtained from a candidate patient, can be subjected to an immune assay, e.g., in situ immunostaining, using an antibody specific to gp130. A cancer patient carrying gp130 negative cancer cells is determined as suitable for the IL-6 treatment of this invention.

Conventional methods, known to those of ordinary skill in the art of medicine, can be used to administer the pharmaceutical composition mentioned above to a cancer patient suitable for the treatment, e.g., administered parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrastemal, intrathecal, intralesional, and intracranial injection or infusion techniques. In addition, it can be administered to the subject via injectable depot routes of administration such as using 1-, 3-, or 6-month depot injectable or biodegradable materials and methods.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

To facilitate delivery, an IL-6 protein can be conjugated with a chaperon agent. As used herein, "conjugated" means two entities are associated, preferably with sufficient affinity that the therapeutic benefit of the association between the two entities is realized. Conjugated includes covalent or noncovalent bonding as well as other forms of association, such as entrapment of one entity on or within the other, or of either or both entities on or within a third entity (e.g., a micelle).

The chaperon agent can be a naturally occurring substance, such as a protein (e.g., human serum albumin, low-density lipoprotein, or globulin), carbohydrate (e.g., a dextran, pullulan, chitin, chitosan, inulin, cyclodextrin or hyaluronic acid), or lipid. It can also be a recombinant or synthetic molecule, such as a synthetic polymer, e.g., a synthetic polyamino acid. Examples of polyamino acids include polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl) methacrylamide copolymer (HMPA), polyethylene glycol (PEG), polyvinyl alcohol (PVA), polyurethane, poly(2-ethylacryllic acid), N-isopropylacrylamide polymers, and polyphosphazine.

In one example, the chaperon agent is a micelle, liposome, nanoparticle, or microsphere, in which the oligonucleotide/interfering RNA is encapsulated. Methods for preparing such a micelle, liposome, nanoparticle, or microsphere are well known in the art. See, e.g., U.S. Pat. Nos. 5,108,921; 5,354,844; and 5,416,016.

In another example, the chaperon agent serves as a substrate for attachment of one or more of a fusogenic or condensing agent.

A fusogenic agent is responsive to the local pH. For instance, upon encountering the pH within an endosome, it can cause a physical change in its immediate environment, e.g., a change in osmotic properties which disrupts or increases the permeability of the endosome membrane, thereby facilitating release of the antisense oligonucleotide into host cell's cytoplasm. A preferred fusogenic agent changes charge, e.g., becomes protonated at a pH lower than a physiological range (e.g., at pH 4.5-6.5). Fusogenic agents can be molecules containing an amino group capable of undergoing a change of charge (e.g., protonation) when exposed to a specific pH range. Such fusogenic agents include polymers having polyamino chains (e.g., polyethyleneimine) and membrane disruptive agents (e.g., mellittin). Other examples include polyhistidine, polyimidazole, polypyridine, polypropyleneimine, and a polyacetal substance (e.g., a cationic polyacetal).

A condensing agent interacts with a protein, causing it to condense (e.g., reduce the size of the oligonucleotide), thus protecting it against degradation. Preferably, the condensing agent includes a moiety (e.g., a charged moiety) that interacts with the protein via, e.g., ionic interactions. Examples of condensing agents include polylysine, spermine, spermidine, polyamine or quarternary salt thereof, pseudopeptide-polyamine, peptidomimetic polyamine, dendrimer polyamine, arginine, amidine, protamine, cationic lipid, cationic porphyrin, and alpha helical peptide.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Example 1

IL-6 Inhibits Growth of Non-hematopoietic Cancer Cells and Promotes Growth of Hematopoietic Cancer Cells To examine the effect of IL-6 on cell growth, the hematopoietic and non-hematopoietic cancer cell lines listed in Table 2 below were cultured following routine procedures in the presence of IL-6 at 20 µg/ml for 6 days. Cell morphology/growth of both IL-6 treated and untreated cells were examined under a microscope. As shown in Table 2, IL-6 inhibits growth of all non-hematopoietic cancer cells but promotes growth of all hematopoietic cancer cells.

TABLE 2

Effect of IL-6 on Growth of Hematopoietic and Non-hematopoietic Cancer Cells

|  | Cancer Cell Lines | Type of Cancer | Effect of IL-6 on Cell Growth |
|---|---|---|---|
| Non-hematopoietic | C3L5 | Breast cancer | Inhibition |
|  | PC-3 | Prostate cancer | Inhibition |
|  | H1299 | non-small cell lung cancer | Inhibition |
|  | A549 |  | Inhibition |
|  | IMC32 | Neuroblastoma | Inhibition |
|  | CoCa2 | Colon cancer | Inhibition |
|  | RCC9 | Renal cellular carcinoma | Inhibition |
|  | NTD1 | Teratoma | Inhibition |
|  | H9 | Hepatitis cellular carcinoma | Inhibition |
|  | SW1573 | Alveolus adenocarcinoma | Inhibition |
|  |  | Choriocarcinoma | Inhibition |
|  | Hela | Cervical cancer | Inhibition |
|  | Mel-28 | melanoma | Inhibition |
|  | Mewo |  | Inhibition |
|  | B16F10 |  | Inhibition |
|  | SCC-25 | Squamous carcinoma cells | Inhibition |
| Hematopoietic | K562 | Leukemia | Promotion |
|  | Jurkat | T-cell lymphoma | Promotion |
|  | NCI H929 | Small cell lung cancer | Promotion |
|  | Mouse bone marrow cells |  | Promotion |

Mel-28, Mewo, SCC-25, B16F10, and Jurkat cells were treated with IL-6 at various concentrations (i.e., 2.5, 5, 10, 20, and 40 μg/ml). As shown in FIG. 1, panels A-E, IL-6 inhibited growth of Mel-28, Mewo, SCC-25, B16F10 and promoted growth of Jurkat cells, both in a dose-dependent manner.

Two melanoma cell lines (Mel-28 and Mewo) and one squamous carcinoma cell line (SCC-25) were treated with IL-6 (20 μg/ml) for one day. The treated cells were washed with PBS and then subjected to lissamine green staining to detect normal cells and Annexin V staining to detect apoptotic cells. As observed under a fluorescence microscope, most untreated cancer cells were normal while a substantial portion of the IL-6 treated cancer cells were apoptotic. This indicates that IL-6 induced apoptosis in non-hematopoietic cancer cells.

Example 2

Treating Breast Cancer with IL-6 in Mice

Breast cancer C3L5 cells were injected into nude mice (6-8 weeks) at 300,000 cells/per mouse. On the same day, some of the injected mice were treated with IL-6 via subcutaneous injection at 100 μg per mouse (early treatment). The remaining mice were treated with IL-6 at the same dosage via the same injection route 7 days after the breast cancer cell injection (late treatment).

Tissue samples were obtained from both early-treated, and late-treated mice three days after IL-6 treatment, as well as from untreated mice. Histochemical analysis was performed to examine cancer cell growth/tumor development in these tissue samples. Growth of cancer cells and lymphocyte infiltration were observed in untreated mice. Differently, no cancer cell growth was observed in the early-treated mice and strong necrosis was observed in the late-treated mice. These results indicate that IL-6 is effective in treating breast cancer at both early stage and late stage.

Example 3

Treating Melanoma with IL-6 in Mice

Mel-28 melanoma cells were injected into nude and C57/B6j mice (6-8 weeks) at 800,000 cells/per mouse. The injected mice were divided into three groups: (1) control group, (2) early-treatment group, and (3) late-treatment group. On the same day of the melanoma cell injection, the mice in the early-treatment group were each administered with 250 μg IL-6 (1 μg/μl) via subcutaneous injection, while the mice in both the control and late-treatment groups were administered with PBS. On the $7^{th}$, $14^{th}$, and $21^{St}$ day after the melanoma cell injection, the mice in both the early-treatment and late-treatment groups were each administered with 250 μg IL-6 via subcutaneous injection and the control mice were injected with PBS. All mice were sacrificed at day 28 and the sizes of the tumors developed in them were measured. The results are summarized in Table 3.

TABLE 3

Tumor Size and weight in IL-6 Treated Mice and Control Mice

| Group | Mouse Number | Tumor Size (mm$^3$) Mean (Std) | Tumor Weight (g) Mean (Std) |
|---|---|---|---|
| Early Treatment | 16 | 146 (291)*** | 0.12 (0.25)‡ |
| Late Treatment | 12 | 6645 (1995)** | 3.59 (0.86)*† |
| Control | 16 | 11402 (4265)* | 5.22 (1.55)* |

*$p < 0.001$ as compared with the early-treatment or control group
†$p < 0.0001$ as compared with the early-treatment group
‡$p < 0.0001$ as compared with both the late treatment group and the control group Tissue samples were obtained from all mice at the cancer cell-injecting sites and subjected to immunohistochemical staining. A large amount of cancerous tissues were observed in the control mice, while only a very low amount of cancerous tissues were observed in the early-treated mice. In the late-treated mice, necrosis and apoptosis were observed in tumor tissues.

Brain tissue samples were also obtained from all of the mice to examine occurrence of cancer metastasis. Brain metastasis was observed in the control mice but not in the mice of the early-treatment group. As to the late-treated mice, cancer cells were detected in brain tissues from these mice; however, a high level of apoptosis was observed in these cancer cells.

Example 4

Identification of Gp 130-Positive and Gp 130-Negative Cancer Cells in Tissue Samples Myeloma and melanoma tissue samples, obtained from human patients, were cultured on a glass microscope slide, washed by PBS, and fixed by a comfix solution for 5 min. The fixed samples were washed 3 times with PBS, 4 min for each wash and then incubated with a rabbit anti-human gp130 antibody (1:100 dilution; purchased from Santa Cruz Biotechnology, Inc.) at room temperature overnight. Afterwards, the tissue samples were washed 3 times with PBS, 5 min for each wash and then incubated with a sheep anti-rabbit IgG antibody that is labeled with a green fluorescent dye (1:250 dilution; purchased from Santa Cruz Biotechnology, Inc.) for 1-2 hours. After being washed for 3 times with PBS, 5 min.

each, the tissue samples were incubated with a blue fluorescent dye for nuclei staining, washed again three times with PBS, dried, and mounted. The tissue samples were then observed under a fluorescence microscope. In the myeloma tissue sample, blue fluorescence was observed at nuclei and green fluorescence on cell surfaces, indicating that myeloma cells express gp130 on their surfaces. By contrast, only blue fluorescence was observed at cell nuclei in the melanoma tissue sample, indicating that this type of cancer cell does not express surface gp130.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method for inhibiting the growth of a non-hematopoietic cancer, comprising contacting the non-hematopoietic cancer with interleukin 6 (IL-6) in an amount effective to inhibit cancer cell growth, wherein the non-hematopoietic cancer is gp130 negative.

2. The method of claim 1, wherein the contacting step is performed by administering the IL-6 to a subject having the non-hematopoietic cancer.

3. The method of claim 1, wherein the non-hematopoietic cancer is breast cancer, ovary cancer, cervical cancer, uterus cancer, testicle cancer, prostate cancer, skin cancer, head and neck cancer, stomach cancer, colon cancer, esophagus cancer, gallbladder cancer, kidney cancer, liver cancer, pancreas cancer, non-small cell lung cancer, brain cancer, bone cancer, neuroblastoma, teratuma, melanoma, Alveolus adeocarcinoma, or choriocarcinoma.

4. The method of claim 2, wherein the non-hematopoietic cancer is breast cancer, ovary cancer, cervical cancer, uterus cancer, testicle cancer, prostate cancer, skin cancer, head and neck cancer, stomach cancer, colon cancer, esophagus cancer, gallbladder cancer, kidney cancer, liver cancer, pancreas cancer, non-small cell lung cancer, brain cancer, bone cancer, neuroblastoma, teratuma, melanoma, Alveolus adeocarcinoma, or choriocarcinoma.

5. The method of claim 4, wherein the non-hematopoietic cancer is breast cancer, prostate cancer, non-small cell lung cancer, colon cancer, stomach cancer, melanoma, liver cancer, pancreatic cancer, cervical cancer, kidney cancer, and brain cancer.

6. The method of claim 1, wherein the IL-6 is human IL-6.

7. The method of claim 2, wherein the IL-6 is human IL-6.

8. The method of claim 2, wherein the composition is administered parenterally.

9. The method of claim 2, wherein the IL-6 is co-administered with another anti-cancer agent.

10. The method of claim 2, wherein the IL-6 is the only active ingredient administered to the subject.

* * * * *